United States Patent [19]

Tummes et al.

[11] 4,299,990

[45] Nov. 10, 1981

[54] PROCESS FOR PREPARING ALDEHYDES

[75] Inventors: Hans Tummes, Oberhausen; Boy Cornils, Dinslaken; Heinz Noeske, Oberhausen, all of Fed. Rep. of Germany

[73] Assignee: Ruhrchemie AG, Oberhausen, Fed. Rep. of Germany

[21] Appl. No.: 164,386

[22] Filed: Jun. 30, 1980

[30] Foreign Application Priority Data

Jul. 13, 1979 [DE] Fed. Rep. of Germany ....... 2928314

[51] Int. Cl.³ ............................................. C07C 45/50
[52] U.S. Cl. .................................... 568/454; 568/882
[58] Field of Search ......................... 568/454, 451, 882

[56] References Cited

U.S. PATENT DOCUMENTS

| | | | |
|---|---|---|---|
| 4,060,557 | 11/1977 | Macalaer, Sr. | 568/454 |
| 4,201,728 | 5/1980 | Hughes | 568/454 |
| 4,215,077 | 7/1980 | Matsumoto | 568/454 |
| 4,230,641 | 10/1980 | Bartish | 568/454 |

FOREIGN PATENT DOCUMENTS 754724 1/1971 Belgium.

Primary Examiner—Werren B. Lone
Attorney, Agent, or Firm—Sprung, Felfe, Horn, Lynch & Kramer

[57] ABSTRACT

A process is described for preparing aldehyde by hydroformylation of olefins, in which the olefins together with carbon monoxide, hydrogen and paraffins are introduced into a solution of rhodium carbonyl-triphenylphosphine complexes as catalyst and phosphines as solvent, the improvement wherein the gas stream entering the catalyst solution contains 5 to 30% by volume of paraffins with 1 to 5 carbon atoms.

6 Claims, 1 Drawing Figure

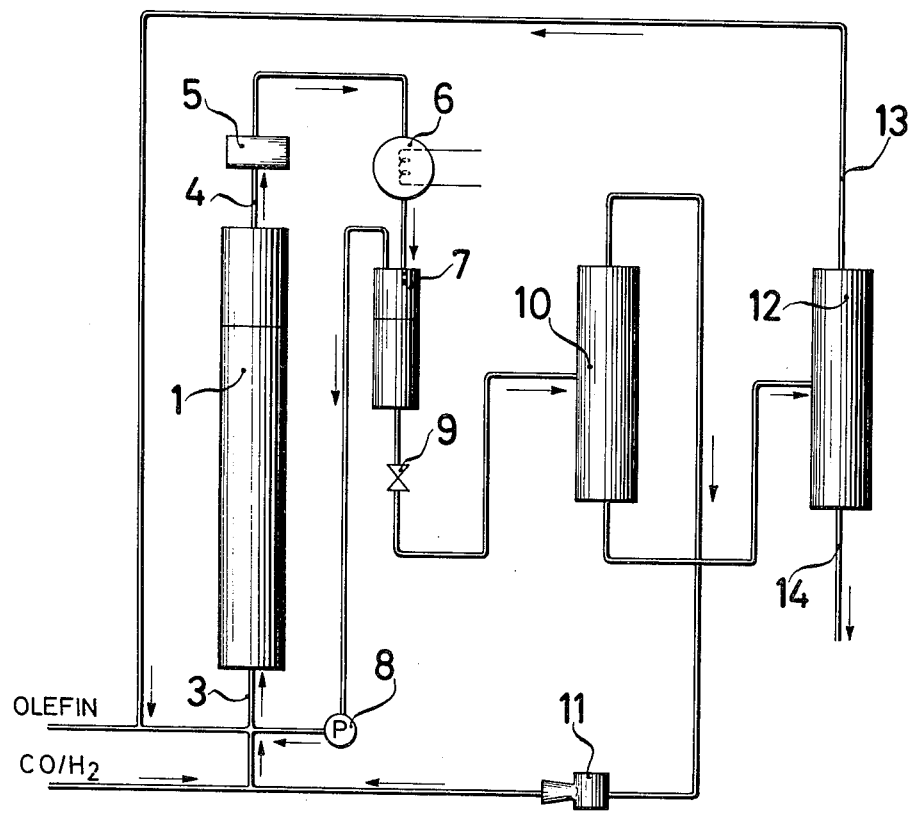

PROCESS FOR PREPARING ALDEHYDES

BACKGROUND OF THE INVENTION

1. Field of the Invention

The present invention relates to an improved process for preparing aldehydes by reacting olefins with carbon monoxide and hydrogen in the presence of rhodium carbonyl compounds containing phosphines as complex ligands.

2. Discussion of Prior Art

The hydroformylation of olefins to aldehyehydes takes place in a substantially more selective manner with rhodium catalysts than with cobalt catalysts. It is thus possible to carry out the oxo synthesis on a technical scale with very small concentrations of rhodium as catalyst. Nevertheless, the economy of this variation of the oxo process is substantially influenced by the use of rhodium since rhodium is about one thousand times more expensive than cobalt. When using rhodium catalysts an effort is therefore made not only to convert the olefin employed to aldehyde, without the formation of by-products, but also to restrict the consumption of catalyst to an absolute minimum.

The selectivity of the hydroformylation in the presence of rhodium catalysts can be improved as regards straight chain aldehydes by using rhodium carbonyls that contain phosphorus ligands. Thus, for example, German Offenlegungsschrift No. 19 39 322 describes the hydroformylation of olefinically unsaturated compounds with hydridocarbonyl-bis (trisubstituted phosphine)-rhodium or hydridocarbonyl-tris(trisubstituted phosphine)-rhodium compounds as catalyst. Trisubstituted phosphines include, inter alia, those containing aryl, alkyl or aralkyl radicals or substituted aryl, alkyl or aralkyl radicals, and phosphites are also mentioned. A basic feature of this process is that the olefinically unsaturated compounds are converted in the liquid phase, in which the reaction products remain after the conversion.

Since the reaction product impairs the activity of the catalyst solution, efforts are made to separate the reaction products and catalyst from one another as quickly as possible.

According to a known procedure, a heterogeneous catalyst system is employed in which the actual catalyst is bonded so firmly to a carrier that it cannot be removed therefrom under the reaction conditions. If the starting substances are brought into contact with the firmly arranged catalyst, the olefin is converted into the catalyst-free reaction product.

Other processes use rhodium carbonyl compounds containing complex ligands as catalyst, which are dissolved in a solvent having a very low vapor pressure. When the gaseous feedstock is passed through the catalyst solution the olefin reacts in the solution with the synthesis gas and the hydroformylation products that are formed, which are liquid per se, are immediately expelled together with the excess gases from the catalyst solution. Such processes are described for example in German Offenlegungsschrift No. 17 68 303 and in U.K. Patent Specification No. 13 87 657.

In all the afore-mentioned hydroformylation processes, in which a catalyst solution consisting of complexed rhodium carbonyls is used, the main problem is the decrease in the activity of the catalyst solutions, which are either recycled or kept stationary in the reactor. As a result of this decrease in activity a proportion of the catalyst solution must either constantly be replaced or the whole catalyst solution must be replaced after a certain time by a new, active solution. The processing of a spent catalyst solution consisting essentially of triphenylphosphine and high molecular weight hydroformylation products is not a simple process on account of the very valuable rhodium contained in the solution. A whole series of methods have in fact been described, according to which it is possible to recover the active Rh catalyst from residues of the oxo synthesis with rhodium-complex catalysts. However, the technical useful effect of this process is very slight and accordingly this process has not achieved any practical significance. In order to restore the full activity of the rhodium catalyst it is necessary to reconvert the rhodium into a pure inorganic rhodium salt, with the removal of all organic constituents of the catalyst solution. Since rhodium losses must be avoided, such procedure can be economically carried out only by means of precious metal separators. This means that a certain amount of rhodium catalyst material is always in the process of being shuttled backwards and forwards for processing between the companies employing the oxo process, and the precious metal processors. In addition to the cost arising from the processing and from the associated rhodium losses, the amount of rhodium being processed at any time represents an additional investment. For this reason it is desirable to prolong the life of the complex rhodium-carbonyl catalysts as long as possible by maintaining a constant activity.

SUMMARY OF THE INVENTION

It has now been found that the activity of hydroformylation catalysts in the form of phosphine-modified rhodium-carbonyls in a phosphine, for example triphenylphosphine as solvent, is less affected if the feedstock, which in general consists of olefins, carbon monoxide and hydrogen, also contains paraffins with 1 to 5 C atoms. The invention thus consists of a process for preparing aldehydes by hydroformylation of olefins, in which the olefins together with carbon monoxide, hydrogen and paraffins are introduced into a solution of rhodium carbonyltriphenylphosphine complexes as catalyst and phosphines as solvent, the hydroformylation products formed and the unreacted feedstock are immediately removed as a gas stream from the catalyst solution, the liquid hydroformylation products are separated from the gas stream by cooling the remaining gaseous reaction products are recycled, mixed with fresh feedstock olefin, carbon monoxide and hydrogen, to the catalyst solution. The process is characterized in that the gas stream entering the catalyst solution contains 5 to 30% by volume of paraffins with 1 to 5 carbon atoms.

Although the partial pressures of carbon monoxide and hydrogen are reduced by the presence of the saturated hydrocarbons in the feedstock gas and circulating gas of the hydroformulation process, there is no reduction in the rate of conversion of the olefins and accordingly for a given reactor volume the productivity of the reactor is not negatively influenced by the presence of the paraffins, despite the additional increase in the gas flow rate through the catalyst solution. Since the residence time of the reaction products in the catalyst solution and thus the formation of higher boiling point compounds is considerably reduced by the fairly high paraffin content in the feedstock gas and circulating gas, the active catalyst system remains substantially free from harmful reaction products and thus retains its full activity over a comparatively long period of time.

BRIEF DESCRIPTION OF DRAWING

The annexed drawing is a flow diagram showing a suitable scheme for carrying out the invention.

DESCRIPTION OF SPECIFIC EMBODIMENT

The reactants are converted in a reactor 1 which contains a catalyst solution 2 and is provided with a cooling system. The catalyst solution is thoroughly mixed by the turbulence-generating gas mixture flowing in from the bottom, with the result that the reactor has the characteristics of a stirred boiler. The reaction products leave the head of the reactor as a gas. The catalyst solution 2 consists of secondary or tertiary phosphines, e.g. triphenylphosphine as solvent, and rhodium-carbonyls containing secondary or tertiary phosphines as further ligands, for example rhodium-carbonyl-triphenylphosphine, as catalyst. The rhodium is used in a concentration of 0.01 to 2%. The gases entering the reactor consists of the olefin to be converted, one or more paraffins, carbon monoxide and hydrogen, as well as smaller proportions of hydroformylation product that was not fully condensed out of the reaction gases from the hydroformylation stage and remains in the recycled circulating gas.

Suitable feedstock olefins are α-unsaturated compounds containing at least one vinyl group of the formula $CH_2=CHR$, in which R can denote the following groups: saturated or unsaturated aliphatic or cycloaliphatic radicals, aryl groups which may contain saturated or unsaturated alkyl groups, and heterocyclic groups. The following compounds may be mentioned as suitable examples; ethylene, propylene, butene-1, pentene-1, hexene-1, heptene-1, octene-1, decene-1, dodecene-1, tetradecene-1, hexadecene-1, octadecene-1, vinylcyclohexane, styrene, vinylpyridine, butadiene and isoprene.

Paraffin hydrocarbons with 1 to 5 C atoms that can be used according to the invention include for example methane, ethane, propane, butane, isobutane, pentane, isopentane and cyclopentane.

The feedstock that flows from below into the reactor 1 through a line 3 reacts within the turbulent catalyst solution to form the hydroformylation products. Reaction products and unreacted feedstock leave in the form of a gas from the head of the reactor through a line 4. The olefins are hydroformylated at a pressure of 1 to 50 atmospheres and at temperatures of 80° to 160° C. The volume ratio of the components of the carbon monoxide/hydrogen mixture is conveniently 1:2 to 2:1. 4 to 50 volumes of $CO/H_2$ mixture are employed per volume of olefin. The paraffin hydrocarbons with 1 to 4 C atoms should be present in an amount of 0.5 to 10 moles per mole of olefin flowing into the catalyst solution. The excess should be greater the higher the molecular weight of the olefin employed. The excess will also depend on the temperature and pressure under which the reaction takes place, and is greater the lower the reaction temperature and the higher the reaction pressure. The olefin content of the total feedstock product entering the catalyst solution should be less than 20% by volume.

In order to prevent liquid particles being entrained with the exiting gas stream, built-in structures, e.g. cyclones 5, are advantageously provided in the waste gas line, which separate the entrained liquid particles and return them to the reactor.

The gases freed from the entrained liquid particles are cooled in a cooler 6 in order to condense the hydroformylation products. In this connection, the cooling temperature is conveniently chosen so that the paraffin hydrocarbon used as carrier gas does not condense out but remains together with the reaction gases (CO and $H_2$) in the residual gas.

The amount of circulating gas per unit volume of catalyst solution depends on the necessity to maintain the catalyst solution in the reactor in a state of constant motion in order to achieve a high transportation of material and thus a high conversion. This means that the amount of gas, referred to normal pressure, that has to be cycled is greater at higher pressures than at lower pressures.

The mixture present after the cooler 6 is separated into gaseous and liquid products in a gas separator 7. The gaseous products are returned to the reactor by means of a gas circulating pump 8. The liquid products, which also contain the reaction gases dissolved at the reaction pressure, are led through a pressure release stage 9 to a degasification column 10. Here the dissolved gases are largely freed from the paraffin hydrocarbon and unconverted olefin fraction and brought to the synthesis pressure in the reactor by means of a booster pump 11 until a fraction remains that is released from the system as waste gas, and are finally recycled to the catalyst solution via the reactor feed line 3.

The sump product from the degasification column is passed for further processing to a distillation stage 12. If the olefin employed is liquid under normal conditions, the unreacted olefin fraction is distilled off at the head of the column and returned to the reactor via a line 13, while hydroformylation product 14 is withdrawn from the sump. When olefins that are gaseous under normal conditions are used, the feed stock product to this column is already substantially free from unreacted olefin and accordingly this column then simply serves to remove the residual gas from the hydroformylation product.

EXAMPLE 1

A solution of 0.2 g of Rh-2-ethyl hexanoate in 0.5 l of triphenylphosphine is added to a 1 liter volume stirred autoclave. The apparatus consisting of the stirred autoclave, cooler, gas separator and gas circulation pump is first of all charged with propane to a pressure of 4 atmospheres and then with synthesis gas ($CO/H_2$ ratio 1:1) to a pressure of 30 atmospheres. The gas mixture (13% propane and 87% synthesis gas) is led by means of the gas circulation pump at a rate of 50 pressure liters/hour through the vigorously stirred Rh-containing triphenylphosphine solution heated to 130° C. The gases leaving the autoclave are cooled to 30° in the cooler to condense out non-gaseous reaction products, and are then returned via the circulation pump to the autoclave.

After establishing the constant reaction conditions, namely a pressure of 30 atmospheres, catalyst solution temperature of 130° C., gas circulation rate of 50 pressure liters/hour, 250 g of propylene and about 20 g of propane are pumped uniformly per hour and by means of the feedstock pumps into the reactor and the pressure in the circulating gas is maintained at a constant value of 30 atmospheres by the inflow of fresh synthesis gas ($CO/H_2$ 1:1). The hydroformylation products formed during the conversion of the propylene in the catalyst solution heated to 130° are removed immediately from the catalyst solution together with the circulating gases, and are condensed out in the cooler from the gas stream and collected in a condensation vessel. The products obtained in the condensation vessel are subjected to a pressure release and transferred to a collection vessel, and both the liquid products and the gaseous products liberated during the pressure release are constantly investigated as regards their composition. The composition of the gas circulating in the apparatus is also determined in the same sequence and the addition of the propane is regulated so that the gas mixture entering the catalyst solution has a propane content of between 10 and 15%. At a constant addition of 250 g of propylene (100%), a catalyst temperature of 130° and a gas circulation rate of 50 pressure liters/hour, the compositions and product amounts shown in the following Table 1 are obtained during the course of a 20-day extended experiment. Pure n-butyraldehyde and i-butyraldehyde can be obtained in a known manner from the resultant liquid product by fractional distillation in selective columns.

TABLE 1

| Products | Day of Experiment | | | | |
|---|---|---|---|---|---|
| | 1 | 5 | 10 | 15 | 20 |
| Composition (Vol. %) of feedstock gas in the catalyst solution (Fresh gas + circulating gas) | | | | | |
| Propylene | 15.8 | 15.3 | 15.6 | 15.4 | 15.2 |
| Propane | 12.7 | 11.6 | 10.9 | 12.4 | 11.5 |
| CO | 35.2 | 36.0 | 36.4 | 35.2 | 36.1 |
| $H_2$ | 36.3 | 37.1 | 37.1 | 37.0 | 37.2 |
| Resultant liquid product amount, g/h | 361 | 358 | 364 | 360 | 361 |
| Composition in % by weight | | | | | |
| Propane | 1.5 | 1.4 | 1.7 | 1.6 | 1.5 |
| Propylene | 1.8 | 1.8 | 2.0 | 1.8 | 1.7 |
| i-$C_4$—al | 10.8 | 11.5 | 11.2 | 11.3 | 11.0 |
| n-$C_4$—al | 85.6 | 84.9 | 84.6 | 85.0 | 85.5 |
| i-$C_4$—ol | 0.1 | 0.1 | 0.1 | 0.1 | 0.1 |
| n-$C_4$—ol | 0.2 | 0.2 | 0.3 | 0.2 | 0.2 |
| higher boiling point compounds | — | 0.1 | 0.1 | — | — |
| Flashed gas from the liquid product, amount in l/h | 40 | 42 | 41 | 39 | 41 |
| Average analysis values of the flashed gases | | | | | |
| Propane | 30 Vol. % | | | | |
| Propylene | 41 Vol. % | | | | |
| CO | 15 Vol. % | | | | |
| $H_2$ | 14 Vol. % | | | | |

The amount of product obtained under constant reaction conditions shows that the conversion of the propylene feedstock in the catalyst solution is just as high after 20 days as on the first day, which indicates that the activity of the catalyst solution remains unchanged.

If the same experiment is carried out without additional charging of propane, the product compositions and product amounts given in Table 2 are obtained. The sharp increase in the propylene content in the circulating gas starting at the 10th day leads to the complete stoppage of the reaction by the 12th day.

TABLE 2

| Products | Day of Experiment | | | |
|---|---|---|---|---|
| | 1 | 5 | 10 | 12 |
| Composition (Vol. %) of feedstock gas in the catalyst solution | | | | |
| (Fresh gas + circulating gas) | | | | |
| Propylene | 15.2 | 14.8 | 20.0 | 65.0 |
| Propane | 1.0 | 1.1 | 0.9 | 0.5 |
| CO | 41.0 | 40.5 | 38.1 | 16.5 |
| $H_2$ | 42.8 | 43.6 | 41.0 | 18.0 |
| Resultant liquid product amount, g/h | 322 | 320 | 258 | — |
| Composition in % by weight | | | | |
| Propylene | 1.8 | 1.9 | 2.2 | — |
| Propane | 0.1 | 0.1 | — | — |
| i-$C_4$—al | 11.8 | 11.5 | 11.3 | — |
| n-$C_4$—al | 85.9 | 86.2 | 86.4 | — |
| i-$C_4$—ol | 0.1 | 0.1 | — | — |
| n-$C_4$—ol | 0.2 | 0.2 | 0.1 | — |
| higher boiling point compounds | 0.1 | — | — | — |
| Flashed gas from the liquid product, amount in l/h | 40.2 | 38.4 | 65.0 | — |
| Composition in % by volume | | | | |
| Propane | 6.0 | 6.2 | 4.0 | — |
| Propylene | 70.0 | 75.0 | 80.0 | — |
| CO | 14.0 | 10.5 | 9.0 | — |
| $H_2$ | 10.0 | 8.3 | 7.0 | — |

On repeating the experiment without the addition of propane in the feedstock gas but using a freshly prepared catalyst solution, the reaction again stops after 11 days, the conditions being maintained the same as in the preliminary experiments, since in this case too the propylene content in the feedstock gas rises to more than 60% as a result of a no longer complete conversion.

The incomplete conversion of the propylene added in a constant amount that occurs after a short time in the absence of propane indicates that the activity of the catalyst solution decreases.

In the following it is shown that the presence of propane in the mixture of the feedstock used in the hydroformylation of propylene with a rhodium-containing solution of triphenylphosphine as catalyst with the simultaneous removal of the hydroformylation products together with the circulating gas leads to a substantially lower concentration of the hydroformylation products (e.g. n-butyraldehyde and i-butyraldehyde) in the catalyst solution than in the absence of propane. Instead of propane, the feedstock gas contains a correspondingly higher proportion of synthesis gas. In the experiment a specific amount of catalyst solution is transferred from the autoclave to a pressure vessel and its pressure is released in a gas separator. The hydroformylation products permanently present in the catalyst solution are determined by investigating the gases dissolved in the catalyst solution and liberated during the pressure release, and by determining the i- and n-$C_4$-aldehydes present in the catalyst sample itself. The following values are obtained:

Experimental conditions as above, with propane

| | Day of Experiment | | | |
|---|---|---|---|---|
| | 1 | 5 | 10 | 15 |
| Propane content in the feedstock gas fed to the autoclave | | | | |
| Propane content | 13.4 | 12.2 | 11.5 | 12.8 |
| Propylene content | 8.4 | 7.8 | 8.2 | 7.9 |
| Content of hydroformylation products in the catalyst solution | | | | |
| n-$C_4$—al % by weight | 1.5 | 1.6 | 1.7 | 1.5 |

-continued

|  | Day of Experiment | | | |
|---|---|---|---|---|
|  | 1 | 5 | 10 | 15 |
| i-C$_4$—al % by weight | 0.08 | 0.1 | 0.1 | 0.1 |

Experimental conditions as above, but with a lower propane content

| Propane content in the feedstock gas fed to the autoclave | | |
|---|---|---|
| Propane content | 2.0 | 2.1 |
| Propylene content | 8.6 | 9.5 |
| Content of hydroformylation products in the catalyst solution | | |
| n-C$_4$—al % by weight | 4.5 | 4.0 |
| i-C$_4$—al % by weight | 0.5 | 0.35 |

The presence of the propane in the circulating gas reduces the amount of reactive aldehydes that are constantly contained in the catalyst solution, and thus prevents a deactivation of the solution and considerably prolongs its life.

EXAMPLE 2

Using the same apparatus and the same reaction conditions as in Example 1, butene-1 instead of propylene is hydroformylated, both with and without the addition of butane. The temperature in the cooler is simply increased to 35° in order to avoid butene-1 and butane condensing out from the gas circulation. The experimental results obtained in long-term tests extending over 21 and 14 days are given in Tables 3 and 4.

TABLE 3

Conversion of butene-1 in the presence of butane
Apparatus as in Example 1
Temperature of the catalyst solution 130°
Pressure 30 atmospheres
Gas Circulation 50 pressure liters/hour
Supply of butene-1 250 g/h

| Products | Day of Experiment | | | |
|---|---|---|---|---|
|  | 1 | 7 | 14 | 21 |
| Composition (Vol. %) of feedstock gas in the autoclave (Fresh gas + circulating gas) | | | | |
| Butene-1 | 14.2 | 15.1 | 15.4 | 14.6 |
| Butane | 13.1 | 13.8 | 13.0 | 23.8 |
| CO | 35.7 | 35.0 | 35.4 | 35.8 |
| H$_2$ | 37.0 | 36.1 | 36.2 | 36.8 |
| Amount of liquid product formed, in g/h | 177 | 278 | 271 | 276 |
| Composition in % by weight | | | | |
| Butane | 5.1 | 6.2 | 4.8 | 6.2 |
| Butene-1 | 6.3 | 7.2 | 5.5 | 7.5 |
| 2-methylbutanal | 11.5 | 11.2 | 12.1 | 10.8 |
| n-pentanal | 76.6 | 74.8 | 76.9 | 75.0 |
| 2-methylbutanol | 0.1 | 0.1 | 0.2 | 0.1 |
| n-pentanol | 0.3 | 0.4 | 0.4 | 0.3 |
| higher boiling point compound | 0.1 | 0.1 | 0.1 | 0.1 |
| Flashed gas, amount in l/h | 60 | 61 | 64 | 62 |
| Average composition of the flashed gas | | | | |
| Butane 43% | | | | |
| Butene-1 47% | | | | |
| CO 6% | | | | |
| H$_2$ 4% | | | | |

The experiment shows that the butene-1 conversion during the course of the experiment does not decrease and thus there is no reduction in the activity of the catalyst solution.

For comparison purposes, the conversion of butene-1 is carried out under otherwise identical conditions but in the absence of butane. The experimental results obtained are shown in Table 4.

TABLE 4

Conversion of butene-1 in the absence of additionally added butane.
Conditions as in Table 3

| Products | Day of Experiment | | | |
|---|---|---|---|---|
|  | 1 | 7 | 14 | 15 |
| Composition (Vol. %) Feedstock gas in the autoclave (Fresh gas + circulating gas) | | | | |
| Butane | 15.0 | 14.2 | 28.8 | 68.7 |
| Butene | 0.5 | 0.4 | 0.5 | 0.2 |
| CO | 42.1 | 42.0 | 35.2 | 15.5 |
| H$_2$ | 42.4 | 43.4 | 35.7 | 15.6 |
| Resultant liquid product, in g/h | 246 | 237 | 142 | — |
| Composition in % by weight | | | | |
| Butane | 0.1 | 0.2 | 0.1 | |
| Butene | 7.5 | 8.5 | 9.8 | |
| 2-methylbutanal | 13.0 | 12.1 | 12.2 | |
| Pentanal | 79.0 | 78.7 | 77.5 | |
| 2-methylbutanol | 0.1 | 0.1 | 0.1 | |
| Pentanol | 0.3 | 0.4 | 0.3 | |
| higher boiling point compounds | — | — | — | — |
| Flashed gas, amount in l/h | 44 | 48 | 70 | |
| Composition in volume % | | | | |
| Butane | 2 | 2 | 1 | |
| Butene-1 | 75 | 73 | 81 | |
| CO | 13 | 14 | 8 | |
| H$_2$ | 10 | 11 | 10 | |

The reaction stops after 9 days when the butene-1 concentration in the gas circulation has risen to over 70% as a result of the decreasing activity of the catalyst solution.

What is claimed is:

1. In a process for preparing an aldehyde by hydroformylation of an olefin in which a gaseous olefin together with gaseous carbon monoxide and gaseous hydrogen is introduced into a solution of a rhodium carbonyl-triphenylphospine complex as catalysts and a phosphine as solvent, an improvement wherein the gas stream entering the catalyst solution contains 5 to 30% by volume of at least 1 parraffin with 1 to 5 carbon atoms.

2. A process according to claim 1 wherein following hydroformylation the hydroformylation products formed and unreacted feedstock are immediately removed as a gas stream from the catalyst solution, liquid hydroformylation products are separated from the gas stream by cooling, and the remaining gaseous reaction product is recycled to the hydroformylation zone after being mixed with fresh feedstock olefin.

3. A process according to claim 1, wherein the hydroformylation is effected at a pressure of 1 to 50 atmospheres and at a temperature of 80° to 160° C.

4. A process according to claim 3, wherein the volume ratio of the components of carbon monoxide to hydrogen is 1:2 to 2:1 and 4 to 50 volumes of CO/H$_2$ mixture are employed per volume of olefin.

5. A process according to claim 3, wherein said paraffin hydrocarbons are present in an amount of 0.5 to 10 mols per mol of olefin which flows through the catalyst solution.

6. A process according to claim 5, wherein the olefin content of the total feedstock product entering the catalyst solution is less than 20% by volume.

* * * * *